(12) United States Patent
Janik et al.

(10) Patent No.: US 11,406,461 B2
(45) Date of Patent: Aug. 9, 2022

(54) DELIVERY SYSTEM AND METHOD FOR DELIVERING MATERIAL TO A TARGET SITE DURING A MEDICAL PROCEDURE

(71) Applicant: Stryker Corporation, Kalamazoo, MI (US)

(72) Inventors: John J. Janik, Hudsonville, MI (US); Robert A. Brindley, Delton, MI (US)

(73) Assignee: Stryker Corporation, Kalamazoo, MI (US)

( * ) Notice: Subject to any disclaimer, the term of this patent is extended or adjusted under 35 U.S.C. 154(b) by 188 days.

(21) Appl. No.: 16/575,879

(22) Filed: Sep. 19, 2019

(65) Prior Publication Data

US 2020/0008893 A1    Jan. 9, 2020

Related U.S. Application Data

(63) Continuation of application No. 15/190,581, filed on Jun. 23, 2016, now Pat. No. 10,492,875.
(Continued)

(51) Int. Cl.
*A61B 34/32* (2016.01)
*A61B 17/88* (2006.01)
(Continued)

(52) U.S. Cl.
CPC .......... *A61B 34/32* (2016.02); *A61B 17/8805* (2013.01); *A61B 34/20* (2016.02);
(Continued)

(58) Field of Classification Search
CPC .... A61B 2034/2046; A61B 2034/2055; A61B 2034/2063; A61B 2034/2065;
(Continued)

(56) References Cited

U.S. PATENT DOCUMENTS 5,199,950 A    4/1993   Schmitt et al.
5,845,646 A *  12/1998  Lemelson ...... A61B 17/320758
                                                    128/899
(Continued)

FOREIGN PATENT DOCUMENTS

WO        02062199 A2    8/2002
WO     2006094156 A2    9/2006
(Continued)

OTHER PUBLICATIONS

Ikuna, Koji et al., "Shape Memory Alloy Servo Actuator System With Electric Resistance Feedback and Application for Active Endoscope", Center for Robotic Systems in Microelectronics, University of California, 1988, pp. 427-430.
(Continued)

*Primary Examiner* — Nilay J Shah
(74) *Attorney, Agent, or Firm* — Howard & Howard Attorneys PLLC

(57) ABSTRACT

A delivery system and methods are disclosed for delivering a material to a target site. A delivery instrument is coupled to a robotic manipulator and comprises a delivery device having a distal tip comprising an opening deliver the material to the target site through the opening. A navigation system tracks the delivery device and the target site and generates position signals. One or more controllers are in communication with the robotic manipulator and the navigation system and define a virtual boundary associated with the target site, wherein the virtual boundary is utilized to constrain movement of the delivery device. The one or more controllers control one or more joint motors of the robotic manipulator to move the distal tip of the delivery device with respect to the virtual boundary based on the position signals from the navigation system.

21 Claims, 6 Drawing Sheets

Related U.S. Application Data

(60) Provisional application No. 62/183,374, filed on Jun. 23, 2015.

(51) Int. Cl.
*A61B 34/00* (2016.01)
*A61B 34/20* (2016.01)
*A61B 34/30* (2016.01)
*A61B 90/00* (2016.01)
*A61M 5/172* (2006.01)
*A61B 34/10* (2016.01)
*A61M 5/142* (2006.01)

(52) U.S. Cl.
CPC .............. *A61B 34/30* (2016.02); *A61B 34/70* (2016.02); *A61B 34/76* (2016.02); *A61B 90/03* (2016.02); *A61B 90/361* (2016.02); *A61M 5/172* (2013.01); *A61B 34/25* (2016.02); *A61B 2034/107* (2016.02); *A61B 2034/2046* (2016.02); *A61B 2034/2051* (2016.02); *A61B 2034/2055* (2016.02); *A61B 2034/2059* (2016.02); *A61B 2034/2063* (2016.02); *A61B 2034/301* (2016.02); *A61M 5/142* (2013.01); *A61M 2205/3334* (2013.01); *A61M 2210/02* (2013.01)

(58) Field of Classification Search
CPC . A61B 2034/2068; A61B 34/30; A61B 34/70; A61B 34/76; A61B 90/03; A61B 90/361; A61B 17/8805; A61B 2034/107; A61B 2034/2051; A61M 5/172; A61M 5/142
See application file for complete search history.

(56) References Cited

U.S. PATENT DOCUMENTS

| | | | |
|---|---|---|---|
| 5,865,744 A * | 2/1999 | Lemelson | A61M 5/427 600/407 |
| 5,919,135 A * | 7/1999 | Lemelson | A61B 6/504 600/407 |
| 6,058,323 A * | 5/2000 | Lemelson | A61B 17/320758 128/925 |
| 6,197,115 B1 * | 3/2001 | Barrey | B05C 13/00 118/681 |
| 6,286,514 B1 * | 9/2001 | Lemelson | A61B 17/320758 128/899 |
| 6,293,282 B1 * | 9/2001 | Lemelson | A61B 17/320758 128/899 |
| 6,757,582 B2 | 6/2004 | Brisson et al. | |
| 8,179,073 B2 | 5/2012 | Farritor et al. | |
| 8,651,046 B1 | 2/2014 | Davancens et al. | |
| 8,652,148 B2 | 2/2014 | Zuhars | |
| 8,801,725 B2 | 8/2014 | Ritter et al. | |
| 8,852,210 B2 | 10/2014 | Selover et al. | |
| 9,119,655 B2 | 9/2015 | Bowling et al. | |
| 9,566,120 B2 | 2/2017 | Malackowski et al. | |
| 9,707,043 B2 | 7/2017 | Bozung | |
| 2002/0045888 A1 * | 4/2002 | Ramans | A61B 34/35 606/1 |
| 2002/0082612 A1 * | 6/2002 | Moll | A61B 34/30 606/130 |
| 2002/0133174 A1 | 9/2002 | Charles et al. | |
| 2003/0092448 A1 | 5/2003 | Forstrom et al. | |
| 2003/0114751 A1 * | 6/2003 | Pedain | G16H 50/50 600/431 |
| 2003/0175410 A1 | 9/2003 | Campbell et al. | |
| 2004/0097805 A1 * | 5/2004 | Verard | A61B 1/00071 600/428 |
| 2004/0171924 A1 * | 9/2004 | Mire | A61B 34/20 600/407 |
| 2005/0261591 A1 * | 11/2005 | Boctor | A61B 8/08 600/462 |
| 2006/0074292 A1 | 4/2006 | Thomson et al. | |
| 2006/0094953 A1 * | 5/2006 | Hartlep | A61B 90/36 600/411 |
| 2006/0095022 A1 * | 5/2006 | Moll | A61B 46/10 606/1 |
| 2006/0111692 A1 * | 5/2006 | Hlavka | A61B 18/1492 604/890.1 |
| 2006/0276775 A1 * | 12/2006 | Rosenberg | A61B 17/00234 606/1 |
| 2007/0043338 A1 * | 2/2007 | Moll | A61B 17/062 606/1 |
| 2007/0078466 A1 * | 4/2007 | Bodduluri | A61B 34/70 606/133 |
| 2007/0106306 A1 * | 5/2007 | Bodduluri | A61B 34/10 606/133 |
| 2007/0167745 A1 * | 7/2007 | Case | A61B 90/36 600/424 |
| 2007/0197896 A1 * | 8/2007 | Moll | A61B 1/00039 600/407 |
| 2007/0244387 A1 * | 10/2007 | Rodriguez Ponce | G16H 20/40 600/411 |
| 2007/0260178 A1 | 11/2007 | Skerven et al. | |
| 2008/0058836 A1 * | 3/2008 | Moll | A61B 17/12172 606/130 |
| 2008/0081982 A1 * | 4/2008 | Simon | A61N 5/1048 600/407 |
| 2008/0097187 A1 * | 4/2008 | Gielen | A61B 34/20 600/409 |
| 2008/0123922 A1 * | 5/2008 | Gielen | A61B 6/5241 382/131 |
| 2008/0167674 A1 * | 7/2008 | Bodduluri | A61M 5/20 606/187 |
| 2008/0255505 A1 * | 10/2008 | Carlson | A61B 34/37 604/95.04 |
| 2008/0294107 A1 * | 11/2008 | Chen | A61B 34/70 604/116 |
| 2009/0005765 A1 * | 1/2009 | Oostman, Jr | A61B 17/32053 606/9 |
| 2009/0024141 A1 * | 1/2009 | Stahler | A61B 34/37 606/130 |
| 2009/0247993 A1 * | 10/2009 | Kirschenman | A61B 34/30 606/1 |
| 2010/0240986 A1 * | 9/2010 | Stiles | A61B 5/415 600/424 |
| 2011/0015484 A1 * | 1/2011 | Alvarez | A61B 34/30 600/109 |
| 2011/0015648 A1 * | 1/2011 | Alvarez | A61B 34/76 606/130 |
| 2011/0028894 A1 * | 2/2011 | Foley | A61B 34/30 604/95.01 |
| 2011/0238083 A1 * | 9/2011 | Moll | A61B 34/76 606/130 |
| 2013/0017564 A1 | 1/2013 | Guillemot et al. | |
| 2013/0060278 A1 | 3/2013 | Bozung et al. | |
| 2013/0131694 A1 | 5/2013 | Farritor et al. | |
| 2013/0197542 A1 | 8/2013 | Bonutti | |
| 2014/0039681 A1 | 2/2014 | Bowling et al. | |
| 2014/0058406 A1 | 2/2014 | Tsekos | |
| 2014/0066955 A1 | 3/2014 | Farritor et al. | |
| 2014/0107471 A1 | 4/2014 | Haider et al. | |
| 2014/0142422 A1 | 5/2014 | Manzke et al. | |
| 2014/0171962 A1 | 6/2014 | Kang | |
| 2014/0200621 A1 | 7/2014 | Malackowski et al. | |
| 2014/0276936 A1 * | 9/2014 | Kokish | A61B 34/30 606/130 |
| 2016/0374770 A1 | 12/2016 | Janik et al. | |

FOREIGN PATENT DOCUMENTS

| | | | |
|---|---|---|---|
| WO | 2007056506 A2 | 5/2007 | |
| WO | 2008134017 A1 | 11/2008 | |
| WO | 2011041439 A2 | 4/2011 | |

(56) References Cited

FOREIGN PATENT DOCUMENTS

| WO | 2013033566 A1 | 3/2013 |
|---|---|---|
| WO | 2014110590 A1 | 7/2014 |

OTHER PUBLICATIONS

International Search Report for PCT/US2016/038941, dated Jun. 23, 2016; 13 pages.

* cited by examiner

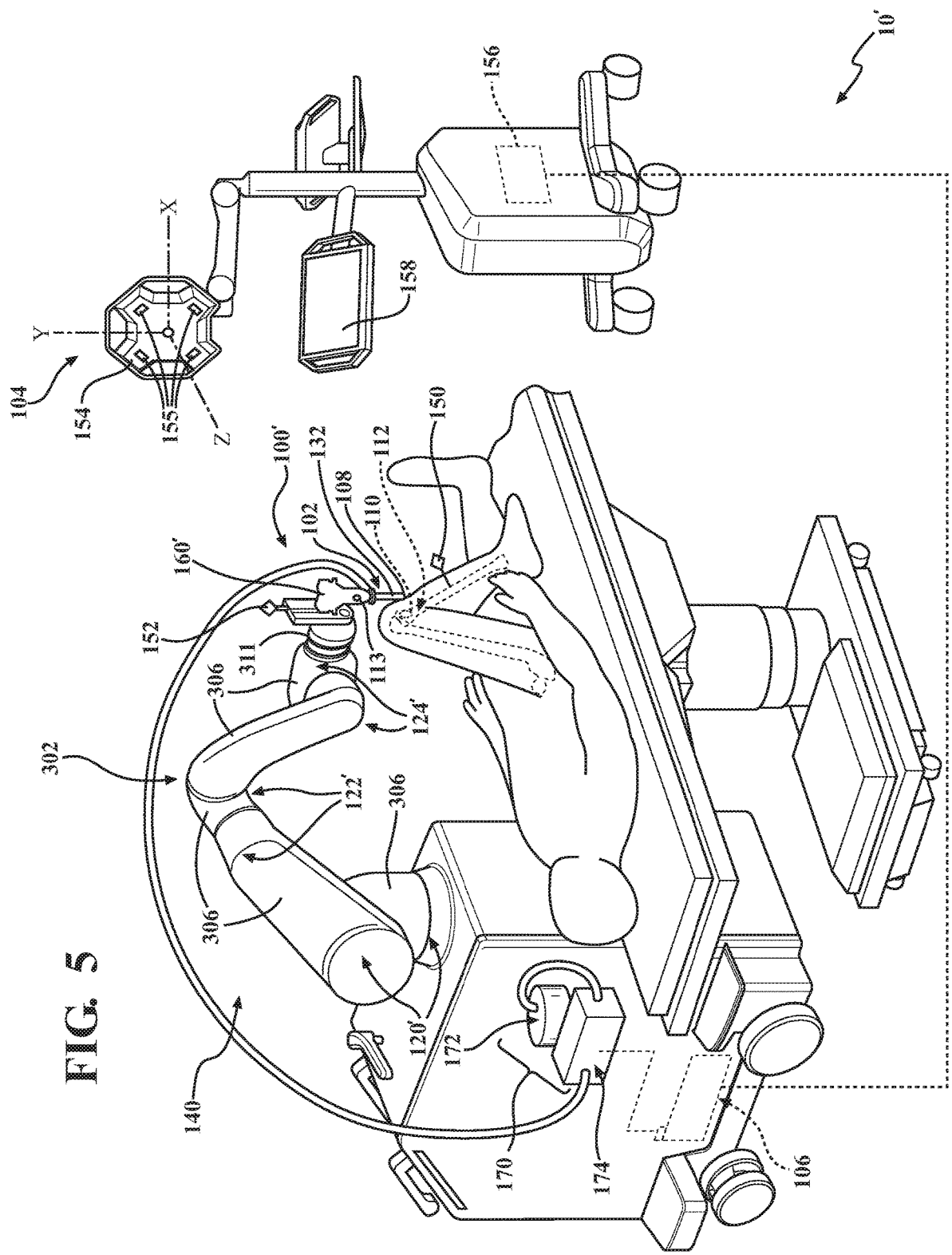

DELIVERY SYSTEM AND METHOD FOR DELIVERING MATERIAL TO A TARGET SITE DURING A MEDICAL PROCEDURE

CROSS-REFERENCE TO RELATED APPLICATION

The subject application is a continuation of U.S. patent application Ser. No. 15/190,581, filed Jun. 23, 2016, now patented as U.S. Pat. No. 10,492,875, which claims the benefit of U.S. provisional patent application No. 62/183,374, filed on Jun. 23, 2015, the disclosure of which is hereby incorporated by reference in its entirety.

TECHNICAL FIELD

The present disclosure relates generally to a delivery system and method for delivering material to a target site during a medical procedure.

BACKGROUND

Delivery systems and methods for delivering a material to a target site during a medical procedure are known in the art. One such delivery system comprises a printhead having a plurality of nozzles through which material is delivered to a target site. A robotic arm positions the printhead relative to the target site. The printhead delivers the material to the target site through the nozzles when the printhead is in position.

Another delivery system comprises a delivery device adapted to dispense a biological material onto a target site. A positioning system positions the target site and the delivery device with respect to one another. A ribbon contains the biological material to be delivered to the target site. The delivery device emits a laser that delivers the biological material from the ribbon onto the target site.

During a medical procedure, however, there is a need in the art to track a position of a target site on a patient as well as to track a position of a delivery device and maintain the position of the delivery device in relation to the target site in order to accommodate movement of the patient during the medical procedure so that the material is delivered in desired patterns, flow rates, and the like with respect to the target site.

SUMMARY

One embodiment of a system for delivering material to a target site during a medical procedure is provided. The delivery system comprises a robotic manipulator comprising a plurality of links and one or more joint motors coupled to the plurality of links. The delivery system comprises a delivery instrument coupled to the robotic manipulator and comprising a delivery device having a distal tip comprising an opening and being configured to deliver the material to the target site through the opening. A navigation system is configured to track the delivery device and the target site and to generate position signals. One or more controllers are in communication with the robotic manipulator and the navigation system and are configured to: define a virtual boundary associated with the target site, wherein the virtual boundary is utilized to constrain movement of the delivery device; and control the one or more joint motors of the robotic manipulator to move the distal tip of the delivery device with respect to the virtual boundary based on the position signals from the navigation system.

One embodiment of a method of operating a delivery system for delivering a material to a target site is provided. The delivery system comprises a robotic manipulator comprising a plurality of links and one or more joint motors coupled to the plurality of links. The delivery system comprises a delivery instrument coupled to the robotic manipulator and comprising a delivery device having a distal tip comprising an opening. The delivery system comprises a navigation system and one or more controllers in communication with the robotic manipulator and the navigation system. The method comprises: tracking, with the navigation system, the delivery device and the target site for generating position signals; defining, with the one or more controllers, a virtual boundary associated with the target site, wherein the virtual boundary is utilized for constraining movement of the delivery device; controlling, with the one or more controllers, the one or more joint motors of the robotic manipulator for moving the distal tip of the delivery device with respect to the virtual boundary based on the position signals from the navigation system; and controlling, with the one or more controllers, the delivery device for delivering the material to the target site through the opening of the delivery device.

One advantage of these embodiments is the ability to track both the delivery device and the virtual boundary and control movement of the opening with respect to the target site and/or control the flow rate of the material based on the position signals from the navigation system while delivering the material to the target site. Likewise, the material being delivered can also be tracked. Furthermore, the virtual boundary provides accurate delivery of the material to the target site by constraining the delivery device, the opening, and/or the material within the virtual boundary. The delivery systems and methods described herein may provide other embodiments not specifically recited herein.

BRIEF DESCRIPTION OF DRAWINGS

Advantages of the present invention will be readily appreciated as the same becomes better understood by reference to the following detailed description when considered in connection with the accompanying drawings wherein:

FIG. 5 is a perspective view of an alternative delivery system for delivering a material to a target site defined by a virtual boundary.

DETAILED DESCRIPTION

Figure 1:
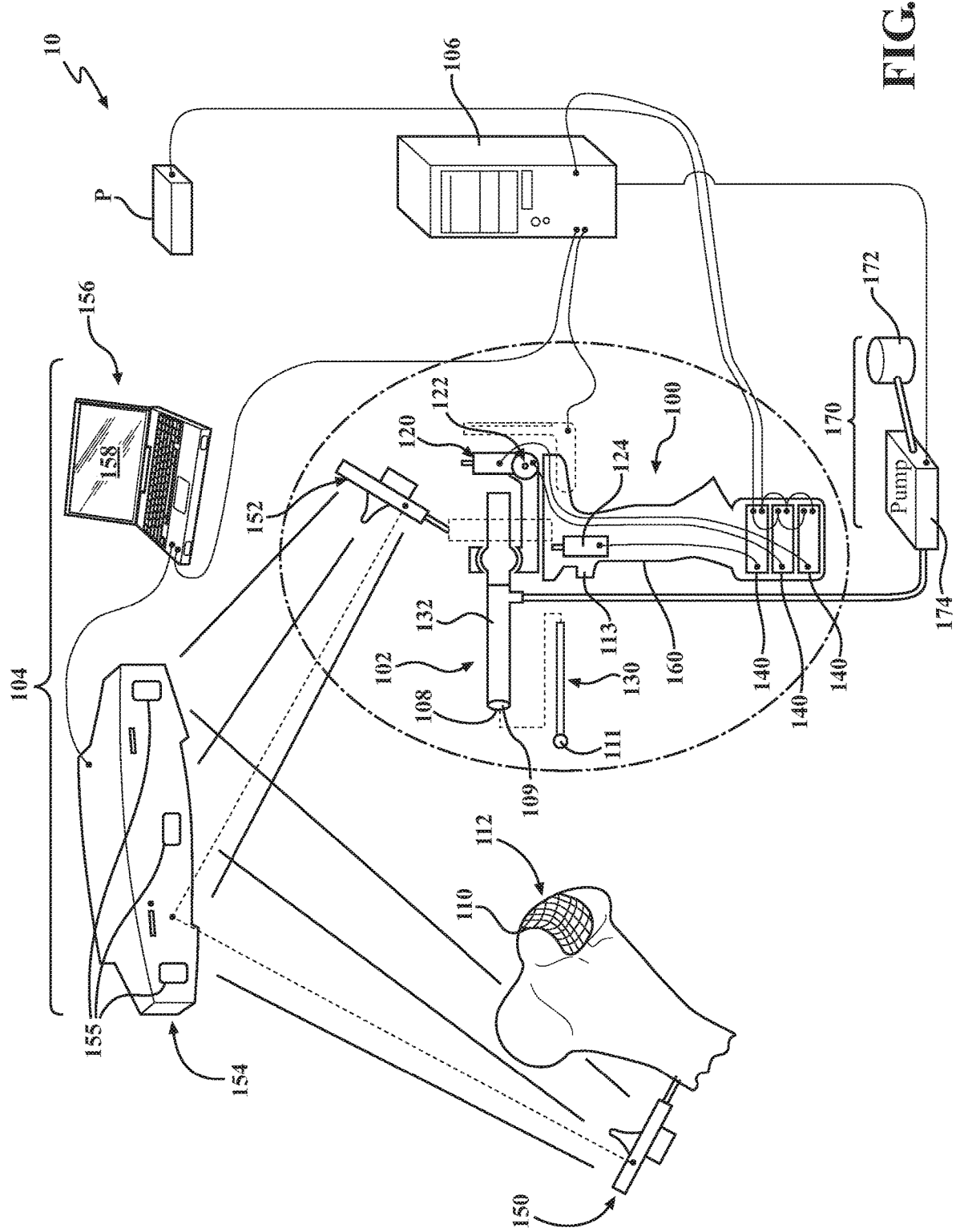
FIG. 1 is a perspective view of a delivery system for delivering a material to a target site.

Referring to the Figures, wherein like numerals indicate like or corresponding parts throughout the several views, a delivery system is shown generally at 10 in FIG. 1.

Figure 2:
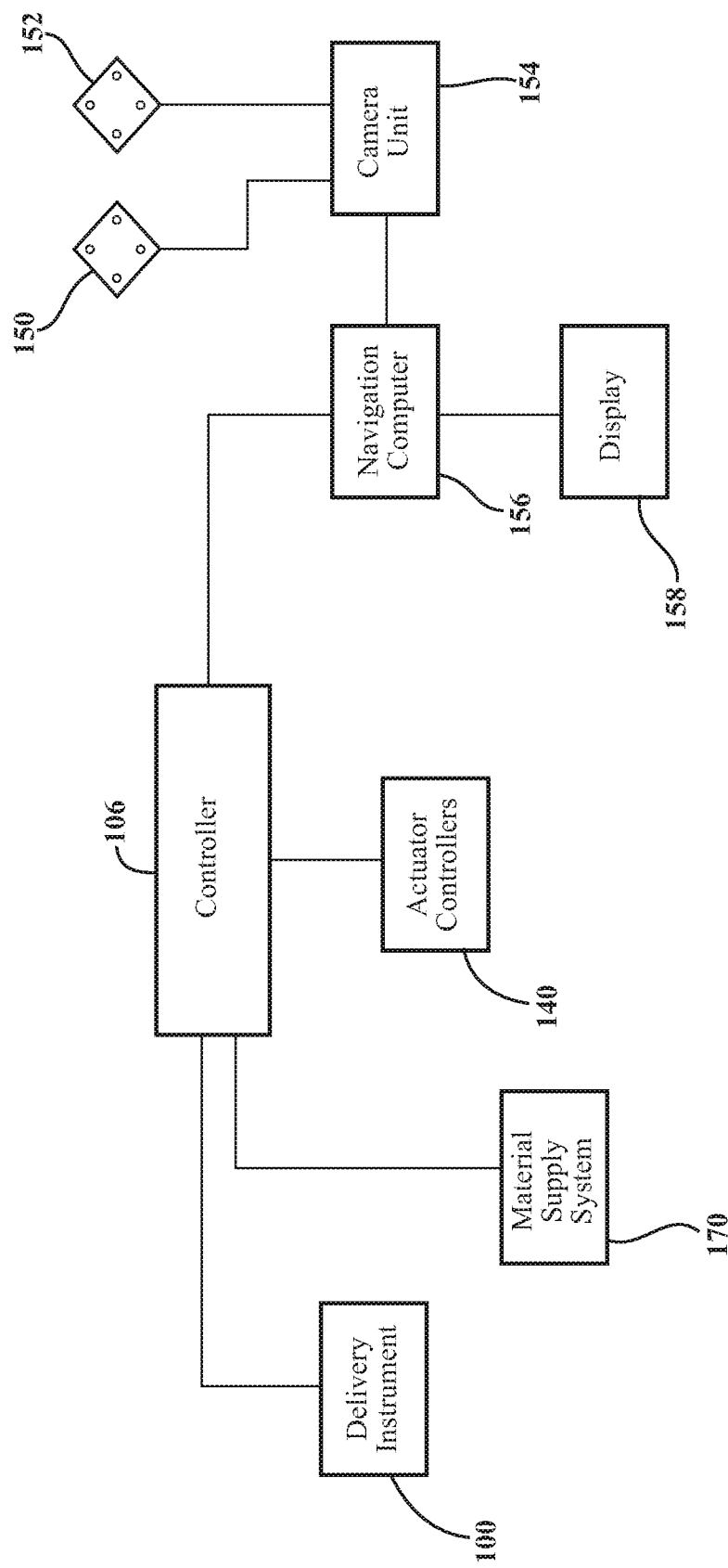
FIG. 2 is a schematic view of the delivery system of FIG. 1.

Referring to FIGS. 1-2, the delivery system 10, according to one embodiment, includes a delivery instrument 100, a delivery device 102, a plurality of actuators 120, 122, 124, e.g. motors, a navigation (localization) system 104, a controller 106, and a material supply system 170. The navigation system 104 tracks the delivery device 102 to keep a distal end tip 108 of the delivery device 102 in a desired relationship to a virtual boundary 110 (herein "distal" means away from an operator supporting the delivery device 102 and toward the virtual boundary 110). A target site 112 of a patient is defined by the virtual boundary 110. The delivery instrument 100 in FIG. 1 is a hand-held device to be grasped by the operator. The delivery instrument 100 may communicate wirelessly with any of the navigation system 104, controller 106, and material supply system 170. Alternatively, the delivery instrument 100 may be wired to any of the same.

In the embodiment shown, the virtual boundary 110 defines a location to which a material should be delivered. The location may be a 3-D space to be at least partially or fully filled with a material, or the location may be a path with respect to which the material should be delivered. The virtual boundary 110 may be defined by any shape or size and may include 2-D or 3-D shapes, lines, trajectories, surfaces, linear paths, non-linear paths, volumes, planes, bore holes, contours, and the like. In some embodiments the virtual boundary 110 can define a 2-D or 3-D boundary across which the distal end tip 108 should not cross. In other embodiments the virtual boundary 110 may define a line, path, trajectory, or course along which the distal end tip 108 should travel. In these cases, the virtual boundary 110 is also referred to as a target path, target trajectory, or target course.

The virtual boundary 110 may be defined with respect to a CT scan, MRI, or other image of the target site. The virtual boundary 110 may thus be defined with respect to a coordinate system of the associated image. Coordinates defining the virtual boundary 110 can then be later transformed into other coordinate systems, as desired, using conventional navigation and transformation methods. In one embodiment, the virtual boundary 110 is generated by and/or implemented by the controller 106. The CT scan, MRI, or other modality may provide a 3-D model of the patient's anatomy and the target site with the virtual boundary 110 being defined as a surface within the 3-D model, a volume in the 3-D model using voxels, or the virtual boundary 110 may be defined using other methods.

The material to be delivered may be any material capable of being delivered, including materials delivered in a flowable condition, such as viscous materials, rigid particles carried in a flowable medium, and the like. The materials may include biological agents, drugs, flowable materials capable of setting to a hardened condition such as soft tissue cements and gels, bone cements, bio-gels, other therapeutic materials, and the like.

In one embodiment, the controller 106 controls the plurality of actuators 120, 122, 124 to move the distal end tip 108 relative to the target site 112. This control locates the distal end tip 108 at a desired location with respect to the virtual boundary 110 to deliver the material in a desired manner. Different control methods for locating the distal end tip 108 at various locations with respect to the virtual boundary 110 are described further below.

Referring to FIG. 1, the delivery device 102 includes a delivery conduit 132 that extends from a proximal end to the distal end tip 108. The delivery conduit 132 defines an opening 109 at the distal end tip 108 through which the material exits the delivery conduit 132 to reach the target site 112. For simplicity, the material may be understood to exit the distal end tip 108, the opening 109, and/or the delivery device 102 generally. Furthermore, because the opening 109 is provided at the distal end tip 108, these terms in some instances may be interchangeable. The proximal end of the delivery conduit 132 is removably attachable to the delivery instrument 100. The proximal end of the delivery conduit 132 may be removably attached to the delivery instrument 100 using a bayonet connection, a threaded coupling, or other connection. The delivery conduit 132 may be a delivery tube, nozzle, and the like. A port may be integrated into the delivery device 102 through which the material may be delivered to the delivery device 102 from the material supply system 170.

In this embodiment, the delivery instrument 100 has a grasping portion 160. The delivery instrument 100 also includes the one or more actuators 120, 122, 124. The actuators 120, 122, 124 are operatively coupled to the delivery device 102 when the delivery device 102 is attached to the delivery instrument 100. The actuators 120, 122, 124 are able to move the distal end tip 108 in at least one or more degrees of freedom, such as pitch, yaw, and/or displacement along an axis with respect to the grasping portion 160.

Each actuator 120, 122, 124 can be controlled by a separate actuator controller 140. In some embodiments, the actuators 120, 122, 124 can be controlled by a single actuator controller 140. In one example, the actuator controllers 140 are wired separately to the actuators 120, 122, 124. In some embodiments, the actuator controllers 140 can be proportional integral derivative (PID) controllers. In some embodiments, the actuator controllers 140 can be integrated with or form part of the delivery device 102. A separate power source P may be in communication with the actuators 120, 122, 124 and actuator controllers 140.

The delivery instrument 100 may be like that shown in U.S. patent application Ser. No. 13/600,888, filed on Aug. 31, 2012, entitled, "SURGICAL INSTRUMENT INCLUDING HOUSING, A CUTTING ACCESSORY THAT EXTENDS FROM THE HOUSING AND ACTUATORS THAT ESTABLISH THE POSITION OF THE CUTTING ACCESSORY RELATIVE TO THE HOUSING," which is hereby incorporated by reference in its entirety.

According to one embodiment, the navigation system 104 includes a first tracker 150, a second tracker 152, a camera unit 154 having a plurality of optical sensors 155, a navigation computer 156, and a display 158. The first tracker 150 is attached to the patient such that the first tracker 150 is in a fixed and known position relative to the target site 112. The second tracker 152 is attached to the delivery instrument 100 such that the second tracker 152 is in a known position relative to the distal end tip 108. For example, the second tracker 152 is fixed relative to the grasping portion 160. The navigation computer 156 is in electrical communication with the display 158. The navigation system 104 may be like that described in U.S. patent application Ser. No. 14/156,856, filed on Jan. 16, 2014, entitled, "Navigation Systems and Methods for Indicating and Reducing Line-of-Sight Errors," which is hereby incorporated by reference in its entirety.

The camera unit 154 senses signals from markers (not shown) on the first tracker 150 and markers (not shown) on the second tracker 152 and sends position signals to the navigation computer 156 corresponding to these markers.

The markers may be active markers such as infrared light emitting diodes or passive markers such as reflector balls, which are conventional in the navigation arts.

The navigation computer 156 interprets the position signals from the camera unit 154 using conventional triangulation and registration methods to determine a position and orientation of the virtual boundary 110 in a camera coordinate system based upon the fixed position of the virtual boundary 110 relative to the first tracker 150.

The navigation computer 156 also interprets the position signals from the camera unit 154 to determine a position and orientation of a known "home" position of the opening 109 in the distal end tip 108 in the camera coordinate system. In one embodiment, the known "home" position of the distal end tip 108 relative to the tracker 152 is measured during manufacture and saved in memory for use by the navigation computer 156 and/or controller 106. Encoders or other position sensors (not shown) are associated with each of the actuators 120, 122, 124. The encoders are in communication with the actuator controllers 140 and the controller 106. The encoders measure deviations of the opening 109 from this known "home" position based on predetermined relationships between actuator movement and movement of the opening 109. As a result, the position and orientation of the opening 109 relative to the tracker 152 can be continuously updated. As such, the encoders may be regarded as subcomponents of the navigation system 104 because the encoder information may be utilized by the navigation system 104 to determine the positions signals related to the opening 109.

The navigation computer 156 generates an image or images of the delivery device 102 (such as an image of the distal end tip 108 and opening 109 therein), the cutting accessory 130, and the target site 112 including the virtual boundary 110 that can be viewed on the display 158 such that the position and orientation of the delivery device 102, including the distal end tip 108 and the position and orientation of the virtual boundary 110 can be viewed in substantially real time during the medical procedure.

In some embodiments the navigation computer 156 sends position signals to the controller 106. The position signals transmit data corresponding to the position and orientation of the virtual boundary 110 and to the position and orientation of the distal end tip 108. The controller 106 controls the actuators 120, 122, 124 to move the distal end tip 108 to ensure that the distal end tip 108 is located in a desired position and/or orientation with respect to the virtual boundary 110 based on the position signals.

Although one embodiment of the navigation system 104 is shown in the Figures, the navigation system 104 may have any other suitable configuration for tracking the position of the delivery device 102, the distal end tip 108 and the target site 112.

In one embodiment, the navigation system 104 is ultrasound-based. For example, the navigation system 104 may comprise an ultrasound imaging device coupled to the navigation computer 156. The ultrasound imaging device images any of the aforementioned objects, e.g., the delivery device 102, the distal end tip 108 and the target site 112 and generates position signals to the controller 106 based on the ultrasound images. The ultrasound images may be 2-D, 3-D, or a combination of both. The navigation computer 156 may process the images in real-time to determine coordinate positioning of the objects. Trackers 150, 152 may be omitted in this embodiment because the ultrasound imaging device may determine position based on the ultrasound images alone. Furthermore, the ultrasound imaging device may have any suitable configuration and may be different than the camera unit 154 as shown in FIG. 1.

In another embodiment, the navigation system 104 is radio frequency (RF)-based. For example, the navigation system 104 may comprise an RF transceiver in communication with the navigation computer 156. Any of the delivery device 102, the distal end tip 108 and the target site 112 may comprise RF emitters or transponders attached thereto. The RF emitters or transponders may be passive or actively energized. The RF transceiver transmits an RF tracking signal and generates position signals to the controller 106 based on RF signals received from the RF emitters. The navigation computer 156 and/or the controller 106 may analyze the received RF signals to associate relative positions thereto. The RF signals may be of any suitable frequency. In this embodiment, there may be no need for any such camera unit 154 as shown in FIG. 1. The RF transceiver may be positioned at any suitable location to effectively track the objects using RF signals. Furthermore, the RF emitters or transponders may have any suitable structural configuration that may be much different than the trackers 150, 152, as shown in FIG. 1.

In yet another embodiment, the navigation system 104 is electromagnetically-based. For example, the navigation system 104 may comprise an EM transceiver coupled to the navigation computer 156. Any of the device 102, the distal end tip 108 and the target site 112 may comprise EM components attached thereto, such as any suitable magnetic tracker, electo-magnetic tracker, inductive tracker, or the like. The trackers may be passive or actively energized. The EM transceiver generates an EM field and generates position signals to the controller 106 based EM signals received from the trackers. The navigation computer 156 and/or the controller 106 may analyze the received EM signals to associate relative positions thereto. Again, such navigation system 104 embodiments may have structural configurations that are different than the navigation system 104 configuration as shown throughout the Figures.

Those skilled in the art appreciate that the navigation system 104 may have any other suitable components or structure not specifically recited herein. Furthermore, any of the techniques, methods, and/or components described above with respect to the camera-based navigation system 104 shown throughout the Figures may be implemented or provided for any of the other embodiments of the navigation system 104 described herein.

Referring back to FIG. 1, the grasping portion 160 is supported by an operator during the medical procedure to deliver the material to the target site 112. The operator can induce movement of the delivery instrument 100 with respect to the virtual boundary 110. In one embodiment, the operator induces movement of the delivery instrument 100 with respect to the virtual boundary 110 by moving the grasping portion 160.

The operator can be a human operator or a robotic operator. The human operator can manually support the grasping portion 160 to manually move the delivery instrument 100. The robotic operator can support the delivery instrument 100 with a robot end effector or a robot manipulator, as will be described below. The robotic operator can induce movement of the delivery instrument 100 with respect to the virtual boundary 110 in response to the position signals from the navigation computer 156 being sent to the controller 106. In some embodiments, the grasping portion 160 can be manually manipulated by the human operator while the instrument 100 is also supported by the robotic operator.

In some embodiments, during the medical procedure, the controller 106 may determine it is appropriate to reposition the distal end tip 108 as the distal end tip 108 approaches, meets, or exceeds the virtual boundary 110. The controller 106 correspondingly controls one or more of the actuators 120, 122, 124 to move the distal end tip 108 in the manner described in U.S. patent application Ser. No. 13/600,888, filed on Aug. 31, 2012, entitled, "SURGICAL INSTRUMENT INCLUDING HOUSING, A CUTTING ACCESSORY THAT EXTENDS FROM THE HOUSING AND ACTUATORS THAT ESTABLISH THE POSITION OF THE CUTTING ACCESSORY RELATIVE TO THE HOUSING," which is hereby incorporated by reference in its entirety. For example, the controller 106 may determine that the distal end tip 108 is crossing the virtual boundary 110 as the distal end tip 108 delivers the material. In response, the controller 106 transmits a signal to at least one of the actuator controllers 140 that causes one or more of the actuators 120, 122, 124 to move the distal end tip 108 away from the virtual boundary 110.

With continued reference to FIG. 1, the material supply system 170 includes a reservoir 172 and a material supply device 174 in communication with the reservoir 172. The reservoir 172 contains the material to be delivered to the target site 112 by the delivery device 102. The material supply device 174 may be a pump or other mechanism for conveying the material from the reservoir 172 to the delivery device 102. The material supply system 170 includes supply lines connecting the reservoir 172 to the material supply device 174 and connecting the material supply device 174 to the port on the delivery device 102. The material supply device 174 is in electrical communication with the controller 106.

The material supply device 174 moves the material to the distal end tip 108 for delivery to the target site 112. In some embodiments the controller 106 controls a flow rate at which the material supply device 174 moves the material to the target site 112. The controller 106 can control the flow rate when the distal end tip 108 approaches, meets, or exceeds the virtual boundary 110. For example, the controller 106 may determine that the distal end tip 108 is crossing the virtual boundary 110 as the distal end tip 108 delivers the material. In response, the controller 106 transmits a signal to the material supply device 174 that causes the flow rate to slow or stop. Although not shown, a variable orifice valve or other type of valve may also be located adjacent to the distal end tip 108 to control the flow of material.

Figure 3A:
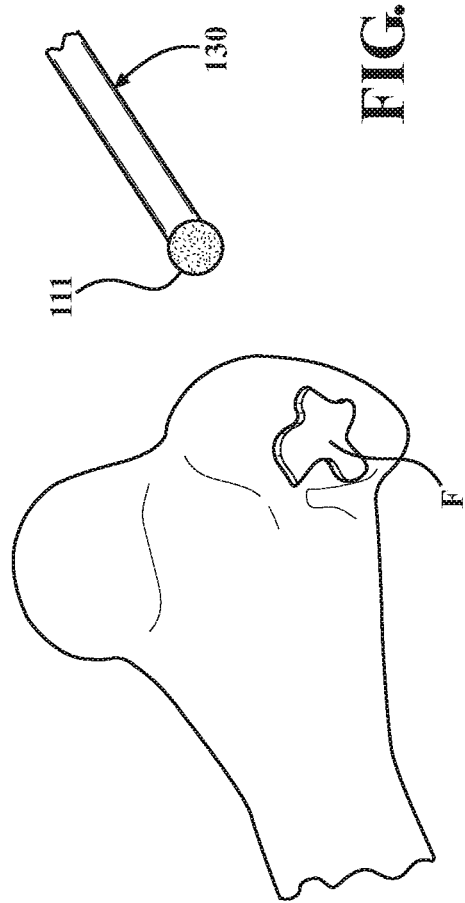
FIG. 3A is an illustration of a target site on a patient and a cutting device being used within a virtual boundary of FIG. 1.

Referring to FIGS. 1 and 3A, in one embodiment, a cutting accessory 130 is first removably attached to the delivery instrument 100 so that the tissue can be removed to define the target site 112 prior to delivering the material to the target site 112. The cutting accessory 130 may include a distal end tip 111 having any suitable configuration, such as a cutting bur, ultrasonic tip, saw, or other accessory or energy applicator suitable for removing tissue. The distal end tip 111 of the cutting accessory 130 is controlled in the same manner as the distal end tip 108 of the delivery device 102 in order to remove the tissue. An example of the cutting accessory 130 and the manner of controlling and moving the same is described in U.S. patent application Ser. No. 13/600, 888, filed on Aug. 31, 2012, entitled, "SURGICAL INSTRUMENT INCLUDING HOUSING, A CUTTING ACCESSORY THAT EXTENDS FROM THE HOUSING AND ACTUATORS THAT ESTABLISH THE POSITION OF THE CUTTING ACCESSORY RELATIVE TO THE HOUSING," which is hereby incorporated by reference in its entirety.

In one embodiment, the delivery device 102 is integrated into the cutting accessory 130. In this case, the cutting accessory 130 defines a central lumen through which the material can be delivered to the target site 112. As a result, removal of the cutting accessory 130 from the delivery instrument 100 and attachment of a separate delivery device 102 is unnecessary. This convenience may be desirable in procedures requiring quicker treatment times or in procedures in which cutting tissue and delivering material can be performed simultaneously.

The delivery instrument 100 may comprise any suitable mechanism for controlling motion of the delivery instrument 100 and/or delivery of the material to the target site 112. In one embodiment, the delivery instrument 100 comprises a button or trigger 113. The trigger 113 may be integrated into the delivery instrument 100, as shown in FIG. 1, or remotely coupled thereto. The trigger 113 may be in communication with any of the actuators 120, 122, 124, the controller 106, and the material supply system 170. The trigger 113 may have several different functions. In some embodiments, the trigger 113 may be a multi-trigger for controlling any of the functions of the delivery instrument 100 described herein.

In one example, depressing and holding the trigger 113 causes the material to be delivered while releasing the trigger 113 stops delivery of material. Alternatively, pressing the trigger 113 once (and releasing) may start the flow of material while pressing the trigger 113 again (and releasing) may stop the flow of material. In either case, pressing the trigger 113 may enable automated control of the delivery of the material as described herein. Additionally, the delivery flow rate of the material may correspond to the extent by which the trigger 113 is depressed. For example, a fully depressed trigger 113 may cause the material to be delivered at a maximum flow rate while a partially depressed trigger 113 may cause the material to be delivered at a partial (less than maximum) flow rate. The human operator or the robotic operator may control the position of the trigger 113 as desired. Furthermore, the trigger 113 may allow the operator to manually control any of the actuators 120, 122, 124 for positioning the distal end tip 108 relative to the target site 112.

Those skilled in the art appreciate that methods other than a button or trigger 113 may be provided to control the aforementioned functions of the delivery instrument 100. For example, in one embodiment, a foot pedal may be coupled to the delivery instrument 100. The operator depresses the foot pedal. Control of the delivery flow rate of the material as a result of depressing the foot pedal may be such as that described above in relation to the trigger 113. For example, depressing the foot pedal and holding the pedal down causes the material to be delivered while releasing the foot pedal stops delivery of material. Alternatively, depressing the foot pedal once (and releasing) may start the flow of material while depressing the foot pedal again (and releasing) may stop the flow of material. Additionally, the delivery flow rate of the material may correspond to the extent by which the foot pedal is depressed. For example, a fully depressed foot pedal may cause the material to be delivered at a maximum flow rate while a partially foot pedal may cause the material to be delivered at a partial (less than maximum) flow rate.

The trigger 113 and/or foot pedal may be utilized for the hand-held instrument 100 or the robotic manipulator 302 as shown in FIG. 5, and as described in detail below.

Figure 3B:
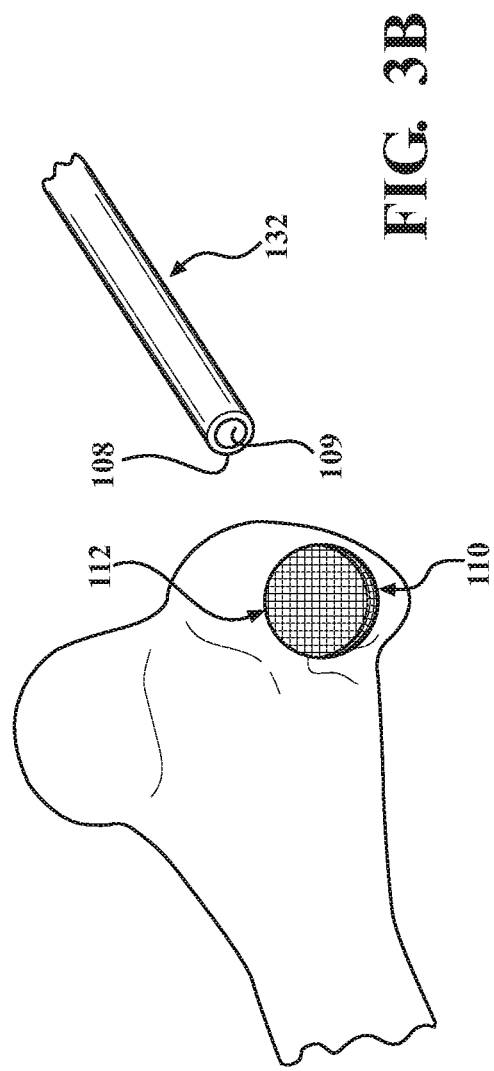
FIG. 3B is an illustration of the target site defined by the virtual boundary and the delivery device of FIG. 1.

FIG. 3A illustrates a procedure in which a focal defect F is located in a femur of a patient. The focal defect F has an irregular shape as shown. In order to treat the focal defect F, tissue such as cartilage and/or bone is removed by the cutting accessory 130 so that a cleaner, better defined 3-D geometric shape defines the target site 112, as shown in FIG. 3B. Once the target site 112 is defined, the material is delivered from the distal end tip 108 of the delivery device to the target site 112. In one embodiment, the material is delivered to the target site 112 so that a final upper surface of the material, once it sets to a hardened condition, matches the original, pre-defect shape of the articular surface of the femur. The upper surface of the hardened material is also flush with the undamaged tissue of the femur surrounding the target site 112.

Figure 4B:
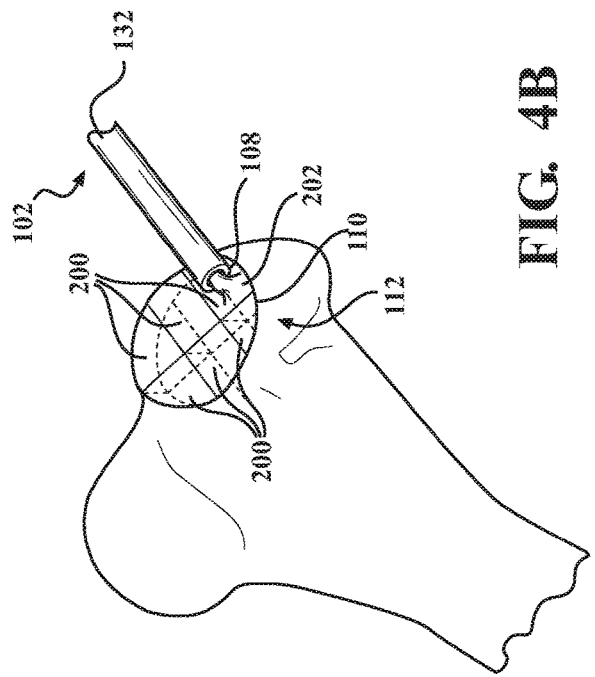
FIG. 4B is an illustration of a target site defined by a virtual boundary according to another embodiment of the present invention.
Figure 4A:
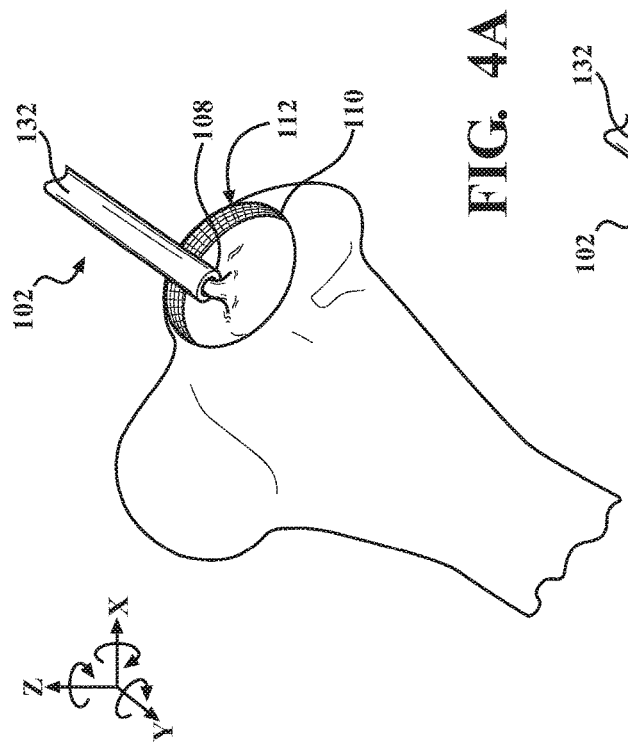
FIG. 4A is an illustration of a target site defined by a virtual boundary according to an embodiment of the present invention.

Referring to FIG. 4A, a first method of delivering material to the target site 112 is shown. The first method comprises the step of the operator moving the distal end tip 108 within the virtual boundary 110. The controller 106 calculates the volume of space defined by the virtual boundary 110 to be filled with the material, or the volume of material to be delivered to the target site 112 is predefined in some other manner prior to the procedure, such as preoperatively or intraoperatively by a surgeon.

The operator freely moves the distal end tip 108 within the virtual boundary 110 while the material is delivered within the virtual boundary 110. To prevent overfilling, the controller 106 stops the delivery device 102 delivering the material to the target site 112 when the volume of the material that has been delivered to the target site 112 is equal to the calculated or predefined volume.

The flow rate of material being delivered from the opening 109 at the distal end tip 108 may also be controlled by the controller 106 (by controlling the material supply device 174 or valve) so that the flow rate is constant, variable, or combinations thereof. The flow rate may also be dependent on the speed with which the operator moves the distal end tip 108 relative to the target site 112. For instance, as the speed increases the flow rate may increase, or as the speed decreases, the flow rate may decrease.

The flow rate may also be controlled by the controller 106 so that the flow rate is constant with respect to movement. In other words, as the operator moves the distal end tip 108 in the virtual boundary 110, the controller 106 measures the speed of the distal end tip 108 and controls the flow rate higher or lower as the speed increases or decreases to accomplish a constant flow rate per unit of movement.

The controller 106 may also be programmed to slow the flow rate of material (by controlling the material supply device 174 or valve) the closer the operator moves the distal end tip 108 to the virtual boundary 110 with the controller 106 stopping the flow of the material should the distal end tip 108 be moved beyond the virtual boundary 110. It should be understood that since the navigation system 104 is also tracking movement of the patient, and thus the virtual boundary 110, the distal end tip 108 may move closer to the virtual boundary 110 by virtue of either the operator expressly moving the distal end tip 108 closer to the virtual boundary 110 or by virtue of patient movement, i.e., the virtual boundary 110 expressly moving closer to the distal end tip 108.

The navigation system 104 and encoders of the instrument 100 track movement of the opening 109 using the methods described in U.S. patent application Ser. No. 13/600,888, filed on Aug. 31, 2012, entitled, "SURGICAL INSTRUMENT INCLUDING HOUSING, A CUTTING ACCESSORY THAT EXTENDS FROM THE HOUSING AND ACTUATORS THAT ESTABLISH THE POSITION OF THE CUTTING ACCESSORY RELATIVE TO THE HOUSING," which is hereby incorporated by reference in its entirety. As the opening 109 moves in the virtual boundary 110, the controller 106 is able to determine the position and orientation of the opening 109 with respect to the virtual boundary 110. The virtual boundary 110 may be determined to be breached by the delivery device 102 should any portion of a perimeter of the delivery device 102 defining the opening 109, cross the virtual boundary 110. Alternatively, the location of a center point of the opening 109 with respect to the tracker 152 is known with the controller 106 tracking movement of the center point with respect to the virtual boundary 110. In this case, the virtual boundary 110 may be defined slightly smaller to account for a radius of the opening 109.

The controller 106 may be programmed to control one or more of the actuators 120, 122, 124 via the actuator controllers 140 to move the distal end tip 108 in one or more degrees of freedom to maintain the distal end tip 108 within the virtual boundary 110 should the operator move the delivery instrument 100 in a way that would otherwise move the distal end tip 108 beyond the virtual boundary 110.

Referring to FIG. 4B, a second method of delivering material to the target site 112 is shown. The second method comprises the step of the operator moving the distal end tip 108 within the virtual boundary 110. The controller 106 calculates the volume of space defined by the virtual boundary 110 to be filled with the material, or the volume of material to be delivered to the target site 112 is predefined in some other manner prior to the procedure, such as preoperatively or intraoperatively by a surgeon.

Once the total volume of material to be delivered is determined, the controller 106, according to one embodiment, segments the space defined by the virtual boundary 110 into a plurality of target subvolumes 200. The total volume of material to be delivered is also separated into a plurality of material subvolumes with each of the material subvolumes assigned to one of the target subvolumes 200. In some cases, the volume of material defined by a material subvolume is equal to the volume of a target subvolume 200 so that the target subvolume 200 is completely filled when the assigned material subvolume is placed within the target subvolume 200. In other embodiments, the volume of material defined by a material subvolume may be less than the volume of a target subvolume 200 so that the target subvolume 200 is less than completely filled.

The operator freely moves the distal end tip 108 within the virtual boundary 110 while the material is delivered to the target site 112. The target subvolume 200 in which the distal end tip 108 is currently positioned is called a current target subvolume 202. To promote desired filling at the target site 112, the controller 106 stops the delivery device 102 delivering the material to the target site 112 when the volume of material that has been delivered while the distal end tip 108 is in the current target subvolume 202 is equal to the material subvolume assigned to the current target subvolume 202. Thus, as the distal end tip 108 is moved within the virtual boundary 110, the controller 106 allows the delivery device 102 to deliver the material until each target subvolume 200 has been filled with the desired material subvolume until the total volume of the material has been delivered to the target site.

In this embodiment, when the operator moves the distal end tip 108 between different target subvolumes 200, the controller 106 keeps a running total of the volume of material delivered to each target subvolume 200 so that the operator may move between the target subvolumes 200 before any of the target subvolumes 200 have completely received the desired material subvolume assigned to them.

This running total is based on the flow rates at which the material supply device 174 supplies the material to each of the target subvolumes 200 and the time for which the material is delivered to the target subvolumes 200 at each flow rate. Volume=flow rate*time.

In this embodiment, the controller 106 may also be programmed to slow the flow rate of material (by controlling the material supply device 174 or valve) the closer the distal end tip 108 moves to the virtual boundary 110 with the controller 106 stopping the flow of the material should the distal end tip 108 move beyond the virtual boundary 110.

Alternatively, the controller 106 may be programmed to control one or more of the actuators 120, 122, 124 via the actuator controllers 140 to move the distal end tip 108 in one or more degrees of freedom to maintain the distal end tip 108 within the virtual boundary 110 should the operator move the delivery instrument 100 in a way that would otherwise move the distal end tip 108 beyond the virtual boundary 110.

Figure 4C:
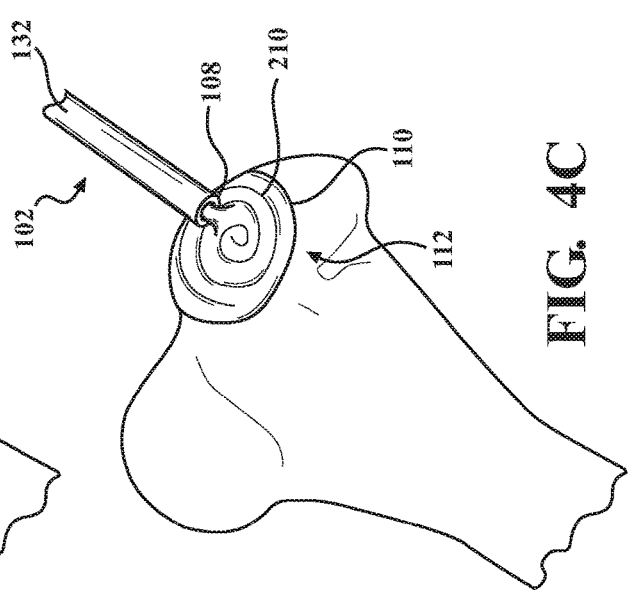
FIG. 4C is an illustration of a target site defined by a virtual boundary according to yet another embodiment of the present invention.

Referring to FIG. 4C, a third method of delivering material to the target site 112 is shown. In this third method, the controller 106 determines a path 210 within the virtual boundary 110 along which the distal end tip 108 is to deliver the material. The path may be defined by a series of coordinates in the camera coordinate system. The operator places the distal end tip 108 generally in a gross location within the virtual boundary 110.

Once the distal end tip 108 is grossly located, the controller 106 actuates one or more of the actuators 120, 122, 124 via the actuator controllers 140 to move the distal end tip 108 autonomously along the path 210 while the operator manually maintains the gross location. The controller 106 controls the flow rate at which the material is delivered to the target site 112 as the distal end tip 108 follows the path 210.

Control of the flow rate may include, for example, controlling the flow rate to be constant along the path 210, or variable along the path 210. Alternatively, different segments of the path 210 may be assigned different predefined flow rates. In this case, the controller 106 controls the material supply device 174 to convey the material at the different, predefined flow rates based on the segment at which the distal end tip 108 is located.

Referring to FIG. 5, an alternative embodiment of the delivery system is shown generally at 10'. In this embodiment, a delivery instrument 100' is attached to a robotic manipulator 302. The delivery system 10' still includes the delivery device 102 removably attached to the delivery instrument 100', a plurality of actuators 120', 122', 124' (joint motors), the navigation system 104, the controller 106, and the material supply system 170.

The robotic manipulator 302 comprises a plurality of linkages 306 forming an arm, and a plurality of active joints (not numbered) for moving the delivery device 102 with respect to the target site 112. The robotic manipulator 302 is operatively coupled to the delivery device 102. A sensor 311, such as a force/torque sensor may be coupled between the delivery instrument 100' and the arm of the robotic manipulator 302 for sensing forces and/or torques applied to the delivery instrument 100' by the operator.

The robotic manipulator 302 may operate in multiple modes including a manual mode and a semi-autonomous mode. An example of a robotic manipulator 302 that can operate in multiple modes is described in U.S. patent application Ser. No. 13/958,070, entitled, "Surgical Manipulator Capable of Controlling a Surgical Instrument in Multiple Modes," the disclosure of which is hereby incorporated by reference. Any of the manual and semi-autonomous control techniques described in U.S. patent application Ser. No. 13/958,070 with respect to manipulating the anatomy using the surgical instrument described therein may be applied fully to dispensing the material on the anatomy using the delivery instrument 100 as described herein.

In the manual mode, the operator grasps a grasping portion 160' of the delivery instrument 100' to deliver the material to the target site 112. The sensor 311 senses the forces/torques applied to the grasping portion 160' and the controller 106 receives signals representative of the sensed forces/torques. The controller 106 is configured to control movement of the delivery instrument 100' and/or the distal end tip 108 via the robotic manipulator 302 in response to the operator's manually applied movements. That is, the actuators 120', 122', 124' are actively driven to move the delivery instrument 100' and/or the distal end tip 108 to the desired position as sensed by the sensor 311 pursuant to the operator's manually applied forces/torques to the grasping portion 160'. The navigation system 104 tracks the delivery device 102 to keep the distal end tip 108 in a desired relationship to the virtual boundary 110. In the manual mode, the operator is able to deliver the material to the target site 112 using the delivery methods described above with respect to FIGS. 4A, 4B, and 4C.

As described above, the robotic manipulator 302, and more specifically, the delivery instrument 100' attached to the robotic manipulator 302 may be equipped with the button or trigger 113. In the manual mode, pressing the trigger 113 allows manual control over the dispensing of the material according to any suitable control, such as those described above.

In the semi-autonomous mode, the robotic manipulator 302 delivers the material autonomously to the target site 112 based on predefined parameters. In the semi-autonomous mode, the controller 106 is configured to autonomously control movement of the delivery instrument 100' and/or the distal end tip 108 via the robotic manipulator 302. The predefined parameters may be, for example, a preprogrammed delivery path or pattern. In one example, the robotic manipulator 302 operates in the semi-autonomous mode with essentially no directional input from the operator.

In order for the robotic manipulator 302 to autonomously displace the delivery device 102, the operator may actuate a command by continually depressing a control button or switch associated with the robot. Upon the negation of the command by the operator, the advancement of the delivery instrument 100' by the robotic manipulator 302 at least temporarily stops. The control button or switch to start autonomous movement of the robotic manipulator 302 may be the trigger 113 or foot pedal as described above.

Additionally or alternatively, when the delivery instrument 100' attached to the robotic manipulator 302 is equipped with the button or trigger 113, pressing the trigger 113 in the semi-autonomous mode may allow manual control over the autonomous dispending of the material according to any suitable control, such as those described above. For example, material may be autonomously dispensed via the robotic manipulator 302 in this mode by pressing the trigger 113 once. Thereafter, the trigger 113 may be pressed again to stop autonomous dispensing of the material via the robotic manipulator 302. Alternatively, material may be autonomously dispensed via the robotic manipulator 302 in this mode by holding down the trigger 113.

In some embodiments, the delivery instrument 100' provides haptic feedback to the operator when the controller 106 determines the operator is attempting to make an undesired movement. One example of an undesired movement includes movement that attempts to move the delivery instrument 100', or distal end tip 108 past the virtual boundary 110. The haptic feedback generally includes any type of feedback alerting the operator's sense of touch. The haptic feedback may include any one or more of force feedback, vibrational feedback, physical repulsion and the like. For example, the delivery instrument 100' may generate vibration energy in the grasping portion 160' or the plurality of actuators 120', 122', 124' may transmit force back to the operator through the grasping portion 160' that is sensed by the operator to alert the operator to keep the distal end tip 108 in a desired location. In some instances, the distal end tip 108 is actuated to move away from the virtual boundary 110 as the distal end tip 108 attempts to exceed limits of the virtual boundary 110. This repulsive movement may be accompanied by haptics to alert the operator of the virtual boundary 110 limits and/or to alert the operator that such repulsion has occurred.

Figure 6:
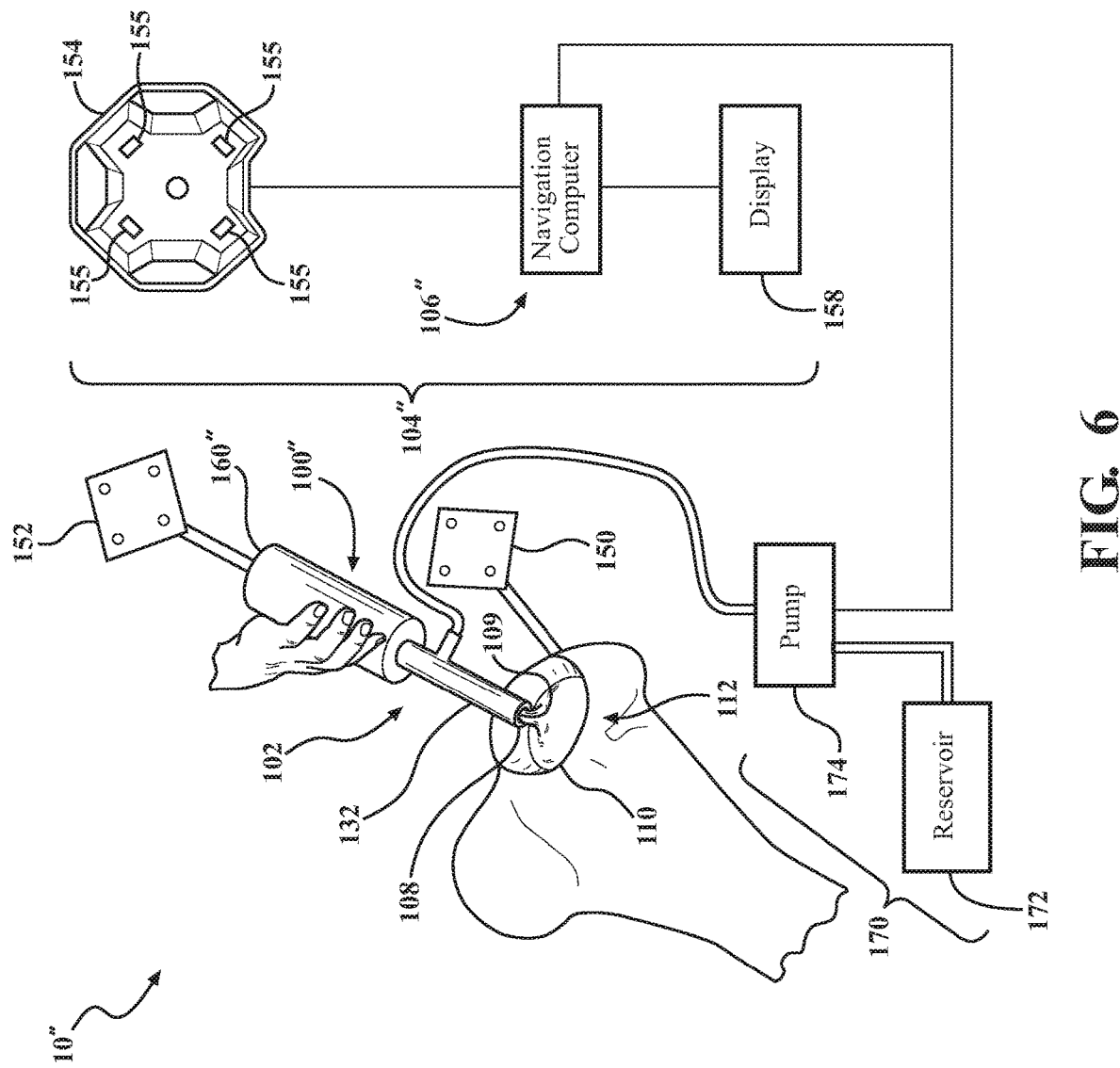
FIG. 6 is a perspective view of a second alternative delivery system for delivering a material to a target site defined by a virtual boundary.

Referring to FIG. 6, a second alternative embodiment of the delivery system is shown generally at 10". In this embodiment, the delivery system 10" includes a delivery instrument 100", the delivery device 102, a navigation system 104", the controller 106", and the material supply system 170 for delivering material to the delivery device 102. Like the prior embodiments, the navigation system 104 tracks the delivery device 102 to keep the distal end tip 108 of the delivery device 102 in a desired relationship to the virtual boundary 110.

In this embodiment, the operator is a human operator that manually supports and moves the delivery instrument 100" directly without any actuators to cause movement of the delivery device 102. The delivery instrument 100" includes the grasping portion 160" for being grasped by the operator. The grasping portion 160" is fixed to the delivery device 102 (and the opening therein) by press fit, adhesive, bayonet connection, threaded connection, or the like. The delivery device 102 may also be integral with the delivery instrument 100" such that the delivery device 102 is a portion of the delivery instrument 100" and the grasping portion is another portion of the delivery instrument 100".

In this embodiment, navigation system 104" includes the same features as the other embodiments except that the controller 106" integrates and combines the functionality of the navigation computer 156 and the controller 106. The controller 106" in this embodiment controls the material supply system 170 using the delivery methods described above with respect to FIGS. 4A, 4B, and 4C. The flow rate may also be controlled in accordance with the examples described above.

In certain embodiments, it may be desired to track the material being delivered from the delivery device 102. For example, the material may ultimately form an implant and a surgeon may wish to visualize construction of the implant during the procedure. Accordingly, the material being delivered may be continuously shown on the display to show the surgeon the progress being made. This may involve tracking the target site, the opening 109 and the flow rate of material and generating corresponding output signals to the display to show a representation of the material that takes into account the position and orientation of the opening 109 during delivery and the amount of material being delivered. The material being delivered may also be color coded with the latest delivered material being represented on the display as one color and older material previously dispensed beforehand being represented on the display by a different color. The target site, such as a bone, is displayed to show the construction of the implant with respect to the target site so that the surgeon can visualize the construction of the implant with respect to the actual anatomy of the patient.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention claimed is:

1. A delivery system for delivering a material to a target site, the delivery system comprising:
a robotic manipulator comprising a plurality of links and one or more joint motors coupled to the plurality of links;
an instrument coupled to the robotic manipulator and comprising a delivery device, the delivery device having a distal tip comprising an opening and being configured to deliver the material to the target site through the opening;
a navigation system being configured to track the delivery device and the target site and to generate position signals; and
one or more controllers in communication with the robotic manipulator and the navigation system and being configured to:
determine a path along which the distal tip is to deliver the material at the target site, wherein the path comprises at least a first path segment and a second path segment;
assign to the first path segment a first predefined flow rate for delivering the material to the target site;
assign to the second path segment a second predefined flow rate for delivering the material to the target site, the first predefined flow rate being different than the second predefined flow rate; and
control the one or more joint motors of the robotic manipulator to move the distal tip of the delivery device along the path based on the position signals from the navigation system.

2. The delivery system of claim 1, wherein the one or more controllers are configured to control the robotic manipulator in a manual mode wherein the one or more controllers are configured to control the one or more joint motors of the robotic manipulator to move the distal tip of the delivery device in response to sensing forces manually exerted by an operator on at least one of the instrument, the delivery device and the robotic manipulator.

3. The delivery system of claim 2, wherein the plurality of links form an arm of the robotic manipulator, and further comprising a force/torque sensor coupled between the instrument and the arm of the robotic manipulator and wherein, in the manual mode, the force/torque sensor is configured to sense forces and/or torques applied to the instrument by the operator.

4. The delivery system of claim 3, wherein the instrument further comprises a grasping portion configured to be manually manipulated by the operator while the instrument is also supported by the robotic manipulator, and wherein the force/torque sensor is configured to sense the forces and/or torques applied to the grasping portion by the operator.

5. The delivery system of claim 2, wherein the instrument is equipped with a button or trigger, and wherein in the manual mode, the one or more controllers are configured to enable manual control over dispensing of the material in response to actuation of the button or trigger.

6. The delivery system of claim 1, wherein the one or more controllers are configured to control the robotic manipulator in a semi-autonomous mode wherein the one or more controllers are configured to control the one or more joint motors of the robotic manipulator to autonomously move the distal tip of the delivery device.

7. The delivery system of claim 6, wherein in the semi-autonomous mode, the one or more controllers are configured to control the delivery device to deliver the material autonomously to the target site based on predefined parameters.

8. The delivery system of claim 1, wherein the one or more controllers are further configured to generate a haptic feedback to an operator through the robotic manipulator.

9. The delivery system of claim 8, wherein the one or more controllers are configured to:
  associate a virtual boundary with the target site, wherein the virtual boundary is utilized to constrain movement of the distal tip: and
  generate the haptic feedback in response to detecting an attempt to move the distal tip beyond the virtual boundary or in response to detecting that the distal tip has crossed the virtual boundary.

10. The delivery system of claim 9, wherein the one or more controllers are configured to control the one or more joint motors of the robotic manipulator to move the distal tip away from the virtual boundary in response to detecting an attempt to move the distal tip beyond the virtual boundary or in response to detecting that the distal tip has crossed the virtual boundary.

11. The delivery system of claim 9, wherein the virtual boundary defines one or more of: a boundary defining a volume into which the material should be delivered; or a boundary for which the distal tip is prohibited from crossing.

12. A method of operating a delivery system for delivering a material to a target site, the delivery system comprising a robotic manipulator comprising a plurality of links and one or more joint motors coupled to the plurality of links, an instrument coupled to the robotic manipulator and comprising a delivery device, the delivery device having a distal tip comprising an opening, a navigation system, and one or more controllers in communication with the robotic manipulator and the navigation system, the method comprising:
  tracking, with the navigation system, the delivery device and the target site for generating position signals;
  determining, with the one or more controllers, a path along which the distal tip is to deliver the material to the target site, wherein the path comprises at least a first path segment and a second path segment;
  assigning to the first path segment, with the one or more controllers, a first predefined flow rate for delivering the material to the target site;
  assigning to the second path segment, with the one or more controllers, a second predefined flow rate for delivering the material to the target site, the first predefined flow rate being different than the second predefined flow rate; and
  controlling, with the one or more controllers, the one or more joint motors of the robotic manipulator for moving the distal tip of the delivery device along the path based on the position signals from the navigation system.

13. The method of claim 12, further comprising the one or more controllers controlling the robotic manipulator in a manual mode for controlling the one or more joint motors of the robotic manipulator for moving the distal tip of the delivery device in response to sensing forces manually exerted by an operator on at least one of the instrument, the delivery device and the robotic manipulator.

14. The method of claim 13, wherein the plurality of links form an arm of the robotic manipulator, and wherein a force/torque sensor is coupled between the instrument and the arm of the robotic manipulator, and further comprising, in the manual mode, sensing forces and/or torques applied to the instrument by the operator utilizing the force/torque sensor.

15. The method of claim 13, wherein the instrument is equipped with a button or trigger, and wherein in the manual mode, the method further comprising the one or more controllers enabling manual control over dispensing of the material in response to actuation of the button or trigger.

16. The method of claim 12, further comprising the one or more controllers controlling the robotic manipulator in a semi-autonomous mode for controlling the one or more joint motors of the robotic manipulator to autonomously move the distal tip of the delivery device.

17. The method of claim 16, further comprising, in the semi-autonomous mode, the one or more controllers controlling the delivery device to deliver the material autonomously to the target site based on predefined parameters.

18. The method of claim 12, further comprising the one or more controllers generating a haptic feedback to an operator through the robotic manipulator.

19. The method of claim 18, further comprising the one or more controllers:
  associating a virtual boundary with the target site, wherein the virtual boundary is utilized for constraining movement of the distal tip; and
  generating the haptic feedback in response to detecting an attempt to move the distal tip beyond the virtual boundary or in response to detecting that the distal tip has crossed the virtual boundary.

20. The method of claim 19 further comprising the one or more controllers controlling the one or more joint motors of the robotic manipulator for moving the distal tip away from the virtual boundary in response to detecting an attempt to move the distal tip beyond the virtual boundary or in response to detecting that the distal tip has crossed the virtual boundary.

21. The method of claim 19, wherein the virtual boundary defines one or more of: a boundary defining a volume into which the material should be delivered; or
  a boundary for which the distal tip is prohibited from crossing.

* * * * *